United States Patent [19]

Reul et al.

[11] 4,331,651

[45] May 25, 1982

[54] DEPOT BODY ON THE BASIS OF SILICONE RUBBER AND PROCESS FOR THE PREPARATION THEREOF

[75] Inventors: Bernhard Reul, Königstein; Dietrich Hiller, Wiesbaden, both of Fed. Rep. of Germany

[73] Assignee: Hoechst Aktiengesellschaft, Frankfurt am Main, Fed. Rep. of Germany

[21] Appl. No.: 113,665

[22] Filed: Jan. 21, 1980

[30] Foreign Application Priority Data

Jan. 23, 1979 [DE] Fed. Rep. of Germany ....... 2902414

[51] Int. Cl.³ .......................... A61K 9/22; A61K 9/52
[52] U.S. Cl. ....................... 424/19; 424/26; 424/184; 424/238; 424/311
[58] Field of Search ............................ 424/19, 26, 184

[56] References Cited

U.S. PATENT DOCUMENTS 3,670,074 6/1972 Doner ................................ 424/184

FOREIGN PATENT DOCUMENTS 2149699 4/1972 Fed. Rep. of Germany ...... 424/184
1991M 9/1963 France ................................ 424/184

OTHER PUBLICATIONS

Pleen et al., J. Amer. Pharm. Ass., vol. XLVI, Dec. 1957, No. 12, Con. No. 24, pp. 705–715.

*Primary Examiner*—Stanley J. Friedman
*Attorney, Agent, or Firm*—Curtis, Morris & Safford

[57] ABSTRACT

Depot body on the basis of silicone rubber for the protracting release of active ingredients which contains from 2 to 50 weight %, relative to silicone rubber, of a release-promoting substance or a corresponding substance mixture in dissolved form, and a process for the preparation of such depot bodies. These depot bodies are suitable especially for the application of active substance onto the mucous membrane of the nasal vestibule of cattle.

14 Claims, No Drawings

DEPOT BODY ON THE BASIS OF SILICONE RUBBER AND PROCESS FOR THE PREPARATION THEREOF

The present invention relates to depot bodies, especially for the treatment of cattle, and a process for the preparation thereof. The depot bodies are suitable for applying active substances to the skin, for example the nasal mucous membrane, of cattle.

It is the object of the invention to provide depot bodies containing active substances which are suitable for administering these active substances over a prolonged period. The depot bodies are to be used especially for administering active substances by means of devices such as described for example in German Pat. No. 2 125 464. For this application, particularly severe requirements are to be met: The active substance(s), dosage thereof and time of administration are fixed by the prevailing medical reasons. The losses of active substance inevitably occurring on application to the mucous membrane of the nasal vestibule must be compensated for by an increased amount of active substance, which, due to the limited space at the point of administration, requires a high concentration of active ingredient in the depot body. Release of the active substance depends on its properties and those of the carrier material, and it should be dosed over a prolonged time, for example 6 weeks to 3 months, at a substantially high rate and in a carefully controlled manner. Residence times of weeks or months have to meet especially severe requirements with respect to the pharmacological tolerability and non-irritating behavior of the substances used. Because of the feed intake habits of cattle, these medicament forms must be resistant during their residence time to nasal secretion and feed components, for example milk feed in the case of calves. Resistance to mechanical strain is furthermore required, because the depot bodies are subjected to such mechanical strain during the long residence time in the nose of the animal. Taking into consideration all these requirements, this form of medicaments must furthermore be generally stable and capable of being economically manufactured.

In accordance with the invention, this object is achieved by providing a depot body on the basis of silicone rubber, which contains, in addition to the active ingredient(s) silicone rubber and optionally solid additives, from 2 to 50 weight %, relative to silicone rubber, of a release-promoting substance or mixture of such substances.

The depot bodies of the invention release the active substance in a predetermined amount per unit of time, while they themselves remain dimensionally stable during practically the full time of administration. The carrier material is based on physiologically acceptable silicone rubber, and it must for example meet defined purity requirements. The auxiliaries to be used, as well as shape and surface characteristics of the depot body are chosen in view of the anatomic conditions at the point of administration, the biopharmaceutical requirements, and the feasibility of economic manufacture.

The depot bodies are especially suitable for administering active substances by means of devices as for example described in German Pat. No. 2 125 464. Such a device is hereinafter called a nose clamp and consists preferably of a bow and two holds for one depot body each.

In addition to the application of active substances to the skin, other forms of administration of the depot bodies of the invention are possible, for example implantation. Furthermore, the composition in accordance with the invention may be injected in the form of the still liquid mass into a tissue, where cross-linking and thus formation of the depot body occurs.

Silicone rubber is distinguished by its chemical indifference, stability, high permeability and moreover easy processing. Other properties of silicone rubber such as insignificant shrinkage and a low coefficient of expansion are favorable for fastening the depot bodies to application devices.

Use of silicone rubber as a carrier for active substances and for influencing the release thereof is known in the art. The silicone rubber employed is preferably vulcanized by means of peroxides, or compounds of tin or platinum. Such forms of medicaments are intended for implantation or introduction into body cavities. The active substances are dissolved or suspended in silicone rubber. These forms of medicaments are of the matrix type or membrane/matrix type (see for example P. J. Dziuk and B. Cook, Endocrinology 78, 208 (1966) and U.S. Pat. No. 3,279,996).

A special form is a matrix of silicone rubber with emulsified hydrophilic solution systems containing the active substances optionally wrapped by a membrane, as described in German Offenlegungsschrift No. 2 547 378.

Because of the severe requirements to be met by the depot body, those on the basis of the above proposals proved to be insufficient.

Among the additives only slightly soluble in water but soluble in silicone rubber, there have been surprisingly found substances which ensure a satisfactory release of active ingredient from the depot body when present in a concentration of from 2 to 50%, relative to silicone rubber. Moreover, these substances either do not affect the mechanical properties of the silicone rubber at all or only to an insignificant extent. The addition thereof reduces the viscosity of the silicone mass and thus allows an increased concentration of active ingredient. This addition is therefore an important condition for the preparation of depot bodies which meet the above requirements in order to ensure a therapeutically active concentration of medicament in the corresponding animal.

Suitable silicone rubbers are especially those on the basis of single-component or two-component systems cross-linked by addition or condensation, for example those on the basis of dimethylpolysiloxane (such as ®Silgel 601 of Wacker Chemie GmbH, Munich, an addition cross-linking two-component composition of 9 parts of component A and 1 part of component B), dimethyldiphenyl-polysiloxane, dimethylpolysiloxanol or silicone copolymers.

The release-inciting, physiologically acceptable additives soluble in silicone rubbers are preferably liposoluble, scarcely hydrosoluble alcohols, esters, ethers and ketones having from 8 to 60 carbon atoms. The depot body contains one or more (that is, a mixture) of these additives.

Release of the active ingredient(s) depends among other things on the concentration of the release-promoting substance or mixture of such substances, and increases as the amount of release-promoting substance dissolved in the silicone rubber increases. For this reason, release-promoting substances are used which have a sufficient solubility in the silicone mass. A further essential criterion resides in the requirement of non-exudation of the release-promoting substances being present in application concentration in the silicone rubber on storage. The concentration is therefore from 2 to 50, preferably 5 to 40, weight %, relative to silicone rubber.

Suitable release-promoting additives include alcohols such as 2-octyldodecanol, oleyl alcohol, phenylethanol; esters such as myristic acid isopropyl ester, caprylic/capric acid laurylstearyl ester, lauric acid hexyl ester (®Cetiol A), propionic acid myristyl ester, isostearic acid ethyl-lauryl ester, oleic acid ethyl ester, acetic acid phenyl ester, benzoic acid benzyl ester, salicylic acid methyl ester, lauric acid mono-1,1-propanediol ester, fatty acid polyethyleneglycol ester, caprylic/capric acid-1,2-propanediol diester (®Miglyol 840), caprylic/capric acid glycerol monoester, lauric acid glycerol diester, butyric acid glycerol triester, caprylic/capric/lauric acid glycerol triester (Miglyol 812), acetic/stearic/oleic acid glycerol triester, adipic acid dibutyl ester, sebacic acid dibutyl ester, phthalic acid ester, citric acid triethyl ester (®Citroflex 2); ethers such as didecyl ether, fatty alcohol polyethyleneglycol ether, alkylaryl polyethyleneglycol ether; anisol; or ketones such as methylnonylketone.

For these reasons, the addition of fatty acid esters of mean molecular weight of the myristic acid isopropyl ester, lauric acid hexyl ester or caprylic/capric acid-1,2-propanediol diester types, or of mean molecular weight ethers of the didecyl ether type is to be preferred.

The addition of such substances inciting the release of active ingredients allows for the administration of active compounds such as anabolic agents to animals in effective doses over prolonged periods by means of a nose clamp without encountering residue problems in the case where the animals are intended for human food.

The depot body may contain one or more active ingredients. The active ingredient is totally or partially wrapped by the silicone rubber, and it may be present in dissolved or disperse form, or in the form of more or less large-size particles either consisting entirely of the active substance or containing it, for example as crystals, granules, powders, with or without further additives. Homogeneous distribution in the silicone rubber is not required: on the contrary, the active substance in undissolved or undispersed form may be present in one or more chambers of the depot body. It may alternatively be present in the depot body in the form of one or more tablets which may contain in addition polyethyleneglycol(s) and further auxiliaries. However, it is recommended that the depot body contains only one tablet which is partially wrapped by the silicone rubber.

The depot bodies of the invention on the basis of silicone rubber are preferably applied to the mucosae, especially by means of a nose clamp. Because of their elasticity, they have the advantage of increasing the total elasticity of the corresponding device, and thus improving the tolerability and anti-irritating properties.

Such forms of medicaments are for example suitable for applying steroid hormones, but they may also be employed for other active substances such as antibiotics, chemotherapeutical agents, prostaglandins or vitamins.

As active substances to be applied to the mucous membrane of the nasal vestibule of cattle, anabolic agents of natural, partially synthetic or synthetic origin are especially interesting, because they aid the formation of flesh and thus improve the butchering quality. Suitable anabolic agents are for example testosterone or trenbolone, optionally in combination with estrogens such as estradiol-17$\beta$. These compounds can be used in the form of alcohols or the derivatives thereof such as esters or ethers (see for example German Offenlegungsschrift No. 2 323 615).

The depot bodies are suitable for the prophylactic and therapeutic treatment of animals.

The depot bodies of the invention may have different shapes, depending on their application. They may be more or less round, cubic or square, cylindrical, oblong, oval, or have any other shape, while their surface may be smooth or structured. When applied to the nasal vestibule, they should be in close contact with the mucous membrane and not hinder respiration. The depot bodies to be applied to the nasal vestibule may be identical or different.

Preparation of the depot bodies comprises dissolving the release-promoting substance(s) in the silicone mass before vulcanization, wrapping, dissolving or dispersing the active ingredient(s), and finally cross-linking.

Composition and preparation of the depot bodies, as well as the examination and the results of the release of active ingredient in vitro are described in Examples 1 to 3. Depending on the size of the animal, that is, of its nasal vestibule, the dimensions of the depot bodies and dosage of the active ingredients may vary from the cited values, which may result furthermore in a modification of the method for determining the release of active ingredient. The examples are merely to illustrate the invention. The activity of the depot bodies of the invention in animal tests is demonstrated in Example 4.

EXAMPLE 1

Preparation of 16 depot bodies (a) 10.712 g of dimethylpolysiloxane (addition cross-linking), component A, were mixed with 2.967 g of caprylic/capric acid-1,2-propanediol diester (corresponding to 20% of release-promoting substance). 1.192 g of dimethylpolysiloxane, component B, were added to this mixture. For aeration purposes, the batch was evacuated with agitation. After interrupting the vacuum, 3.200 g of microfine testosterone and 0.320 g of microfine estradiol-17$\beta$ were placed on the surface of the silicone mixture, and it was again evacuated. Subsequently, the solids in the silicone mixture were dispersed by agitation. The operations as described proceeded at room temperature and were terminated within 10 minutes. The agitation speed was 250 rpm at most. Subsequently, the mass was cast in molds. Tempering was carried out for 30 minutes at 70° C., and the current was then switched off. The depot body had a cylindrical shape, a diameter of 15 mm and a height of 8 mm, a weight of 1.15 g corresponding to a content of 0.2 g of testosterone and 0.02 g of estradiol-17$\beta$. The upper face of the depot body had the form of a spherical cap. The lower face was covered by a plate of plastic material having fastening devices. Further compositions of depot bodies are listed in Tables 3.1 to 3.5.

EXAMPLE 2

Preparation of 16 depot bodies 21 g of trenbolone acetate microfine, 4 g of estradiol-17$\beta$ (free alcohol) microfine and 26.7 g of polyethyleneglycol 4000 powder type were mixed, precompressed, granuled through a sieve of 1.5 mm and compressed to give two-face tablets having a diameter 11 mm.

10.876 g of dimethylpolysiloxane (addition cross-linking), component A, were mixed with 0.636 g of caprylic/capric/lauric acid glycerol triester (corresponding to 5% of release-inciting substance). 1.208 g of dimethylpolysiloxane, component B, were added. For aeration, the batch was evacuated with agitation for 5 minutes.

A tablet was placed on a plate of plastic material provided with a fastening device, and wrapped with the aerated silicone mixture in a suitable mold. Tempering was carried out for 60 minutes at 40° C., and the current was then switched off. The thickness of the silicone rubber layer was 2 mm. The depot body had a cylindrical shape, a diameter of 15 mm and a height of 8 mm, a weight of 1.0535 g corresponding to a content of 0.125 g of trenbolone acetate and 0.02 g of estradiol-17β. The upper face had the form of a spherical cap. The lower face was covered by a plate of plastic material having fastening devices. Further compositions are listed in Table 3.6.

EXAMPLE 3

Method for testing in vitro the release of active ingredient from depot bodies containing from 210 to 280 mg of acetate or from 200 to 469 mg of testosterone, optionally in combination with from 40 to 60 mg of estradiol-17β and estradiol diacetate, respectively.

250 ml of water were charged each to Erlenmeyer flasks having a nominal volume of 300 ml. They were closed by means of ground glass stoppers provided with a fastening device for the holds of the depot bodies at the part facing the interior of the flasks. The fastening device had a length which ensured that the depot bodies were immersed in the water and that their distance from the bottom of the flask was 1 cm. The flasks were agitated at +38.5° C. in an incubation shaking machine (for example air bath of Messrs. Braun or water bath of Messrs. Infors) at a frequency of 200/min.

The water used for elution was replaced daily. The content of testosterone and trenbolone acetate, respectively, was determined by spectrophotometry directly in the extract, optionally after dilution with water. After having united the extracts of one week and concentrated them on an ion exchanger column, the content of estradiol-17β was determined by colorimetry with dansyl chloride.

The results with respect to release of active substance from depot bodies of the invention having a different composition are listed in the following Tables. For a comparison, there is furthermore indicated in these Tables the release from a depot body without addition of a release-promoting substance.

Table 3.1

Comparison of testosterone release in vitro from silicone rubber type Silgel 601 containing dissolved, scarcely hydrosoluble substances. The data are relative to two depot bodies each of identical volume and identical surface (see Example 1)

TABLE 3.1.1

| Composition | mg | mg | mg | mg |
|---|---|---|---|---|
| Testosterone (free alcohol) microfine | 200 | 200 | 300 | 300 |
| Estradiol-17β (free alcohol) microfine | 40 | 40 | 60 | 40 |
| 2-Octyl-dodecanol | — | 115 | — | — |
| Caprylic/capric/lauric acid glycerol ester | — | — | — | 63 |
| Silgel 601 | 1950 | 1945 | 1240 | 1197 |
| Total weight | 2190 | 2300 | 1600 | 1600 |

| Testosterone release in vitro | mg | mg | mg | mg |
|---|---|---|---|---|
| within 1 day | 4 | 9 | 10 | 12 |
| within 4 days | 10 | 19 | 20 | 29 |
| within 11 days | 19 | 36 | 34 | 51 |
| within 14 days | — | — | 40 | 57 |
| within 15 days | — | — | 41 | 59 |

TABLE 3.1.2

| Composition | mg | mg | mg | mg | mg | mg | mg | mg | mg(+) | mg | mg | mg | mg | mg |
|---|---|---|---|---|---|---|---|---|---|---|---|---|---|---|
| Testosterone (free alcohol) microfine | 400 | 400 | 400 | 400 | 400 | 400 | 400 | 400 | 400 | 400 | 400 | 400 | 400 | 469 |
| Estradiol-17β (free alcohol) microfine | 40 | 40 | 40 | 80 | 40 | 40 | 40 | 40 | 40 | 80 | 40 | 40 | 80 | 38 |
| Myristic acid isopropyl ester | — | 93 | 372 | — | — | — | — | — | — | 182 | — | — | — | — |
| Lauric acid hexyl ester | — | — | — | 364 | — | — | — | — | — | — | — | — | — | — |
| Caprylic/capric acid laurylstearyl ester | — | — | — | — | 93 | 372 | — | — | — | — | — | — | — | — |
| Caprylic/capric acid-1,2-propanediol ester | — | — | — | — | — | — | 186 | 279 | 332 | 182 | — | — | — | — |
| Adipic acid dibutyl ester | — | — | — | — | — | — | — | — | — | — | 93 | — | — | — |
| Sebacic acid dibutyl ester | — | — | — | — | — | — | — | — | — | — | — | 93 | — | — |
| Phthalic acid dioctyl ester | — | — | — | — | — | — | — | — | — | — | — | — | 91 | — |
| Didecyl ether | — | — | — | — | — | — | — | — | — | — | — | — | — | 436 |
| Silgel 601 | 1860 | 1767 | 1488 | 1456 | 1767 | 1488 | 1674 | 1581 | 1328 | 1456 | 1767 | 1767 | 1729 | 1307 |
| Total weight | 2300 | 2300 | 2300 | 2300 | 2300 | 2300 | 2300 | 2300 | 2100 | 2300 | 2300 | 2300 | 2300 | 2250 |

| Testosterone release in vitro | mg | mg | mg | mg | mg | mg | mg | mg | mg | mg | mg | mg | mg | mg |
|---|---|---|---|---|---|---|---|---|---|---|---|---|---|---|
| within 1 day | 13 | 16 | 32 | 21 | 14 | 28 | 24 | 21 | 20 | 20 | 19 | 16 | 14 | 28 |
| within 4 days | 28 | 35 | 79 | 58 | 29 | 70 | 52 | 48 | 74 | 62 | 45 | 41 | 28 | 69 |
| within 11 days | 48 | 56 | 137 | 101 | 47 | 112 | 79 | 83 | 135 | 109 | 69 | 73 | 50 | 118 |
| within 14 days | 52 | 61 | 152 | 114 | 52 | 124 | 87 | 92 | 151 | 123 | 76 | 83 | 53 | 133 |
| within 15 days | 54 | 63 | 157 | — | 55 | 129 | 90 | 102 | 168 | — | 78 | 86 | 55 | 138 |
| within 21 days | 65 | 68 | 184 | — | 60 | 152 | 106 | 120 | 187 | — | 89 | 102 | 67 | 164 |

(+)"G"

Table 3.2

Comparison of testosterone release in vitro from silicone rubber on the basis of an addition cross-linking two-component system on the basis of dimethyl-diphenylpolysiloxane (hereinafter called Silicone SLM 71260) containing dissolved, scarcely hydrosoluble substances. The data are relative to two depot bodies each having identical volume and identical surfaces (see Example 1).

TABLE 3.2.1.

| Composition | mg | mg | mg | mg |
|---|---|---|---|---|
| Testosterone (free alcohol) microfine | 300 | 300 | 300 | 300 |
| Caprylic/capric acid glycerol ester | — | 260 | — | — |
| Caprylic/capric/lauric acid glycerol ester | — | — | 260 | — |
| Caprylic/capric acid-1,2-propanediol ester | — | — | — | 260 |
| Silicone SLM 71260 | 1300 | 1040 | 1040 | 1040 |
| Total weight | 1600 | 1600 | 1600 | 1600 |
| Release of active substance in vitro | mg | mg | mg | mg |
| within 1 day | 20 | 22 | 20 | 22 |
| within 4 days | 45 | 76 | 71 | 81 |
| within 14 days | 81 | 158 | 145 | 154 |

TABLE 3.2.2.

| Composition | mg | mg |
|---|---|---|
| Testosterone (free alcohol) microfine | 300 | 400 |
| Caprylic/capric acid-1,2-propanediol ester | | |
| Silicone SLM 71260 | 1040 | 960 |
| Total weight | 1600 | 1600 |
| Release of active substance in vitro | mg | mg |
| within 1 day | 22 | 31 |
| within 4 days | 81 | 93 |
| within 14 days | 154 | 178 |
| within 21 days | 180 | 207 |

TABLE 3.2.3.

| Composition | mg | mg | mg | mg | mg | mg | mg+ | mg |
|---|---|---|---|---|---|---|---|---|
| Testosterone (free alcohol) microfine | 400 | 400 | 400 | 400 | 400 | 400 | 400 | 400 |
| Estradiol-17β-(free alcohol) microfine | — | 40 | — | 40 | — | — | 40 | 80 |
| Estradiol-17β-diacetate microfine | 52 | — | 52 | — | 52 | 52 | — | — |
| Caprylic/capric acid 1,2-propanediol ester | — | — | 369 | 372 | 554 | 739 | 664 | — |
| Lauric acid-hexyl ester | — | — | — | — | — | — | — | 364 |
| Silicone SLM 71260 | 1848 | 1860 | 1479 | 1488 | 1294 | 1109 | 996 | 1456 |
| Total weight | 2300 | 2300 | 2300 | 2300 | 2300 | 2300 | 2100 | 2300 |
| Testosterone release in vitro | mg | mg | mg | mg | mg | mg | mg | mg |
| within 1 day | 15 | 15 | 22 | 22 | 21 | 21 | 23 | 21 |
| within 4 days | 36 | 41 | 76 | 80 | 79 | 83 | 80 | 70 |
| within 14 days | 68 | 75 | 142 | 142 | 146 | 173 | 177 | 138 |
| within 16 days | 74 | 81 | 152 | 153 | 159 | 191 | 202 | 150 |
| within 28 days | — | 117 | — | — | 207 | 257 | 285 | — |
| within 43 days | — | 141 | — | — | 254 | 315 | 357 | — |

+ = "F"

TABLE 3.3

Comparison of trenbolone acetate release in vitro from silicone rubber type Silgel 601 containing dissolved, scarcely water-soluble substances. The data are relative to two depot bodies each having identical volume and identical surfaces (see Example 1).

| Composition | mg | mg | mg | mg | mg | mg | mg |
|---|---|---|---|---|---|---|---|
| Trenbolone acetate microfine | 210 | 210 | 210 | 210 | 210 | 210 | 210 |
| Estradiol-17β (free alcohol) microfine | 40 | 40 | 40 | 40 | 40 | 40 | 40 |
| Myristic acid isopropyl ester | — | 103 | 410 | — | — | — | — |
| Caprylic/capric acid laurylstearyl ester | — | — | — | 103 | — | — | — |
| Caprylic/capric/lauric acid glycerol ester | — | — | — | — | 103 | — | — |
| Caprylic/capric acid-1,2-propanediol ester | — | — | — | — | — | 410 | — |
| Adipic acid dibutyl ester | — | — | — | — | — | — | 103 |
| Silgel 601 | 2050 | 1947 | 1640 | 1947 | 1947 | 1640 | 1947 |
| Total weight | 2300 | 2300 | 2300 | 2300 | 2300 | 2300 | 2300 |
| Trenbolone acetate release in vitro | mg | mg | mg | mg | mg | mg | mg |
| within 1 day | 15 | 10 | 13 | 11 | 20 | 20 | 17 |
| within 4 days | 48 | 50 | 63 | 47 | 60 | 70 | 59 |
| within 14 days | 109 | 115 | 153 | 113 | 123 | 158 | 126 |
| within 21 days | 139 | 137 | 184 | 133 | — | 174 | — |
| within 28 days | 158 | — | — | — | — | — | — |
| within 42 days | 189 | — | — | — | — | — | — |

TABLE 3.4.1

Comparison of estradiol-17β release in vitro from silicone rubber type Silgel 601 containing dissolved, scarcely hydrosoluble substances. The date are relative to two depot bodies each having identical volume and identical surfaces (see Example 1).

| Composition | mg | mg | mg | mg | mg+ | mg | mg | mg |
|---|---|---|---|---|---|---|---|---|
| Testosterone (free alcohol) microfine | 400 | 400 | 400 | 400 | 400 | 400 | 400 | 469 |
| Estradiol-17β (free alcohol) microfine | 40 | 40 | 80 | 40 | 40 | 40 | 40 | 38 |
| Myristic acid isopropyl ester | — | 372 | — | — | — | — | — | — |
| Lauric acid hexyl ester | — | — | 364 | — | — | — | — | — |
| Caprylic/capric acid laurylstearyl ester | — | — | — | 372 | — | — | — | — |
| Caprylic/capric acid-1,2-propanediol ester | — | — | — | — | 332 | — | — | — |
| Adipic acid dibutyl ester | — | — | — | — | — | 93 | — | — |
| Sebacic acid dibutyl ester | — | — | — | — | — | — | 93 | — |
| Didecyl ether | — | — | — | — | — | — | — | 436 |
| Silgel 601 | 1860 | 1488 | 1456 | 1488 | 1328 | 1767 | 1767 | 1307 |
| Total weight | 2300 | 2300 | 2300 | 2300 | 2100 | 2300 | 2300 | 2250 |
| Estradiol 17β release in vitro | mg | mg | mg | mg | mg | mg | mg | mg |
| within 1 week | 1.10 | 4.62 | 5.72 | 4.26 | 5.64 | 2.62 | 2.50 | 3.72 |
| within 2 weeks | 1.72 | 8.16 | — | 7.88 | 10.30 | 3.56 | 3.78 | 5.74 |
| within 3 weeks | 2.26 | 10.34 | — | 10.82 | 13.80 | 4.18 | 4.96 | 7.82 |
| within 4 weeks | 3.02 | 12.64 | — | — | 16.56 | — | — | 9.62 |
| within 5 weeks | 3.36 | — | — | — | 19.04 | — | — | 10.96 |
| within 6 weeks | 4.34 | — | — | — | 20.94 | — | — | 12.46 |

+ = "G"

TABLE 3.4.2

Comparison of estradiol-17β release in vitro from silicone rubber type SLM 71 260 containing dissolved, scarcely hydrosoluble substances. The data are relative to two depot bodies each having identical volume and identical surfaces (see Example 1).

| Composition | mg | mg | mg | mg | mg | mg+ |
|---|---|---|---|---|---|---|
| Testosterone (free alcohol) microfine | 400 | 400 | 400 | 400 | 400 | 400 |
| Estradiol-17β microfine | 40 | 80 | 40 | 40 | 40 | 40 |
| Lauric acid hexyl ester | — | 364 | — | — | — | — |
| Acetic/stearic/oleic acid glycerol ester | — | — | — | 93 | — | — |
| Caprylic/capric acid-1,2-propanediol ester | — | — | 93 | — | 372 | 664 |
| Silicon SLM 71260 | 1860 | 1456 | 1767 | 1767 | 1488 | 996 |
| Total weight | 2300 | 2300 | 2300 | 2300 | 2300 | 2100 |
| Estradiol-17β release in vitro | mg | mg | mg | mg | mg | mg |
| within 1 week | 3.10 | 6.52 | 3.96 | 4.68 | 6.26 | 6.48 |
| within 2 weeks | 4.12 | 11.68 | 6.24 | 7.96 | 11.28 | 13.76 |
| within 3 weeks | 5.58 | 15.86 | 8.34 | 9.84 | — | 19.54 |
| within 4 weeks | 7.74 | — | — | — | — | 24.56 |
| within 5 weeks | 8.62 | — | — | — | — | 29.08 |
| within 6 weeks | 10.16 | — | — | — | — | 32.84 |

+ = "F"

TABLE 3.5

Comparison of estradiol-17β release in vitro from silicone rubber type Silgel 601 containing dissolved, scarcely hydrosoluble substances. The data are relative to two depot bodies each having identical volume and identical surfaces (see Example 1).

| Composition | mg | mg | mg | mg | mg | mg |
|---|---|---|---|---|---|---|
| Trenbolone acetate microfine | 210 | 210 | 210 | 210 | 210 | 210 |
| Estradiol-17β microfine | 40 | 40 | 40 | 40 | — | — |
| Estradiol-17β diacetate microfine | — | — | — | — | 52 | 52 |
| Caprylic/capric/lauric acid glycerol ester | — | 103 | — | — | — | 102 |
| Caprylic/capric acid-1,2-propanediol ester | — | — | 410 | — | — | — |
| Myristic acid-1,2-propyl ester | — | — | — | 410 | — | — |
| Silgel 601 | 2050 | 1947 | 1640 | 1640 | 2038 | 1936 |
| Total weight | 2300 | 2300 | 2300 | 2300 | 2300 | 2300 |
| Release of active substance in vitro | mg | mg | mg | mg | mg | mg |
| within 1 week | 0.44 | 1.96 | 2.18 | 2.44 | 1.36 | 1.90 |
| within 2 weeks | 1.08 | 3.32 | 4.42 | 4.32 | 2.66 | 3.26 |
| within 3 weeks | 1.76 | — | 6.30 | 6.0 | 4.28 | — |
| within 4 weeks | 2.30 | — | — | — | 5.76 | — |
| within 5 weeks | 2.70 | — | — | — | 7.18 | — |
| within 6 weeks | 3.08 | — | — | — | 8.68 | — |

TABLE 3.6

Comparison of trenbolone acetate release in vitro through a layer of 2 mm of silicone rubber type Silgel 601 and Silicone SLM 71 260, respectively, containing dissolved, scarcely hydrosoluble substances. The data of the Table are relative to two depot bodies of the same kind (see Example 2).

| Composition | mg | mg | mg | mg |
|---|---|---|---|---|
| Tablet | | | | |
| Trenbolone acetate microfine | 210 | 210 | 210 | 210 |
| Estradiol-17β (free alcohol) microfine | 40 | 40 | 40 | — |
| Estradiol-17β diacetate microfine | — | — | — | 52 |

TABLE 3.6-continued

Comparison of trenbolone acetate release in vitro through a layer of 2 mm of silicone rubber type Silgel 601 and Silicone SLM 71 260, respectively, containing dissolved, scarcely hydrosoluble substances. The data of the Table are relative to two depot bodies of the same kind (see Example 2).

| | | | | |
|---|---|---|---|---|
| Polyethyleneglycol 4000 | 267 | 267 | — | — |
| Polyethyleneglycol 6000 | — | — | 267 | 255 |
| Silicone layer | | | | |
| Caprylic/capric/lauric acid glycerol ester | — | 79 | — | — |
| Caprylic/capric acid-1,2-propanediol ester | — | — | — | 636 |
| Silgel 601 | 1590 | 1511 | — | — |
| Silicone SLM 71260 | — | — | 1590 | 954 |
| Trenbolone acetate release in vitro | mg | mg | mg | mg |
| within 1 day | 4 | 4 | 4 | 13 |
| within 4 days | 12 | 14 | 17 | 57 |
| within 14 days | 42 | 49 | 51 | 138 |
| within 21 days | 59 | 77 | 75 | 193 |
| within 28 days | 84 | 103 | 107 | 236 |
| within 35 days | 105 | 125 | — | — |
| within 42 days | 130 | 152 | — | — |

EXAMPLE 4

Activity test on milk-fattened store calves using depot bodies as indicated in Tables 3.1.2 "G" and 3.2.3 "F", respectively, for testosterone, and 3.4.1 "G" and 3.4.2 "F", respectively, for estradiol-17$\beta$.

Test operation

Nose clamps according to German Pat. No. 2 125 464 containing depot bodies were applied to 2 groups of 7 milk-fattened store calves each having an average weight of 75.4 and 74.8 kg, respectively, and left at their place for 6 weeks. A third group of 6 calves having an average weight of 76.5 kg remained untreated and served as control. For observing the weight development, the calves were weighed 3 times in intervals of 14 days, and the daily weight increase and the feed utilization (feed consumption:weight increase) per group during the time of treatment was calculated.

Results

The results of daily weight increase, feed utilization and cumulative weight development of groups 1–3 (3 = control group) are listed in the following Tables.

Average values of daily weight alteration in g and %

| | Time | | | | | |
|---|---|---|---|---|---|---|
| Group | 1. and 2. week | | 3. and 4. week | | 5. and 6. week | |
| 1 n = 7 corr. to "G" | 1377 | 126% | 1337 | 153% | 1133 | 129% |
| 2 n = 7 corr. to "F" | 1367 | 125% | 1327 | 152% | 1255 | 143% |
| 3 n = 6 Control | 1095 | 100% | 869 | 100% | 881 | 100% |

Average feed utilization per group during the 6 weeks' test periods

| Group 1 n = 7 corr. to "G" | Group 2 n = 7 corr. to "F" | Group 3 n = 6 Control |
|---|---|---|
| 1.45 | 1.44 | 1.81 |
| +19.9% | +20.6% | ±0 |

Cumulative weight development in kg and %

| Average weight increase in time | Group 1 n = 7 corr. to "G" | | Group 2 n = 7 corr. to "F" | | Group 3 n = 6 Control | |
|---|---|---|---|---|---|---|
| up to 2. week | 19.3 | 126.1% | 19.1 | 124.8% | 15.3 | 100% |
| up to 4. week | 38.0 | 138.2% | 37.7 | 137.1% | 27.5 | 100% |
| up to 6. week | 53.9 | 135.4% | 55.3 | 138.9% | 39.8 | 100% |

The results demonstrate that using depot bodies corresponding to "G" and "F", administered by means of the nose clamp, a weight increase superior to that of a control group (group 3) by 14.1 and 15.5 kg/calf, respectively, is obtained, and furthermore a feed utilization increase of about 20% as compared to the control.

The individual results of cumulative weight development were statistically obtained by comparison in pairs in the T test according to Student (P smaller than 0.01).

What is claimed is:

1. A depot body on a silicone rubber carrier for the prolonged release of an active ingredient which comprises 2 to 50% by weight, based on the silicone rubber carrier, of a release-promoting substance or mixture thereof which is physiologically acceptable and only slightly soluble in water but soluble in silicone rubber, wherein said substance is an alcohol selected from the group consisting of 2-octyldodecanol, oleyl alcohol and phenylethanol, or an ester selected from the group consisting of myristic acid isopropyl ester, caprylic/capric acid laurylstearyl ester, lauric acid hexyl ester, propionic acid myristyl ester, isostearic acid ethyl-lauryl ester, oleic acid ethyl ester, acetic acid phenyl ester, benzoic acid benzyl ester, salicylic acid methyl ester, lauric acid mono-1,1-propanediol ester, fatty acid polyethyleneglycol ester, caprylic/capric acid-1,2-propanediol diester, caprylic/capric acid glycerol monoester, lauric acid glycerol diester, butyric acid glycerol triester, caprylic/capric/lauric acid glycerol triester, acetic/stearic/oleic acid glycerol triester, adipic acid dibutyl ester, sebacic acid dibutyl ester, phthalic acid ester, citric acid triethyl ester, or an ether selected from the group consisting of didecyl ether, fatty alcohol polyethyleneglycol ether, alkyl-aryl polyethyleneglycol ether and anisol or a ketone such as methylnonylketone.

2. The depot body of claim 1 wherein said release-promoting substance is selected from the group consisting of myristic acid isopropyl ester, lauric acid hexyl ester, caprylic/capric acid-1,2-propanediol diester or didecyl ether.

3. The depot body of claim 1 wherein said release-promoting substance is present in an amount of 5 to 40% by weight.

4. The depot body of claim 1 wherein said silicone rubber carrier is a single-component or two-component system cross-linked by addition or condensation.

5. The depot body of claim 1 wherein said silicone rubber carrier is dimethylpolysiloxane, dimethyldiphenylpolysiloxane or dimethylpolysiloxanol.

6. The depot body of claim 1 wherein said active ingredient is in dissolved or dispersed form and is at least partially wrapped in said silicone rubber carrier.

7. The depot body of claim 1 wherein said active ingredient is present in one or more chambers of said depot body.

8. The depot body of claim 1 wherein said active ingredient is present in said depot body in the form of a tablet.

9. The depot body of claim 8 wherein said tablet contains an effective amount of polyethyleneglycol.

10. The depot body of claim 1 wherein said active ingredient is selected from the group consisting of steroids, antibiotics, chemotherapeutic agents, prostaglandins and vitamins.

11. The depot body of claim 1 wherein said active ingredient is testosterone and esters thereof or trenbolone and esters thereof.

12. The depot body of claim 11 wherein said active ingredient is in admixture with estrogens.

13. The depot body of claim 1 adapted to effectively cooperate with a suitable device for applying said depot body to the mucous membrane of the nasal vestibule of cattle.

14. A process for the preparation of a depot body on a suitable silicone rubber carrier for the sustained release of an active ingredient which comprises dissolving 2 to 50% by weight, based on the silicone rubber carrier, of a release-promoting substance as defined in claim 15 in a silicone mixture prior to vulcanization, dissolving, dispersing or wrapping said active ingredient with said silicone rubber carrier and then vulcanizing said silicone rubber carrier.

* * * * *